United States Patent [19]

Castelijns et al.

[11] Patent Number: 5,438,143
[45] Date of Patent: Aug. 1, 1995

[54] PROCESS FOR THE PREPARATION OF SUBSTITUTED PYRIDINES VIA 1-AZA-1,3-BUTADIENES AND THE 1-AZA-1,3-BUTADIENE INTERMEDIATES

[75] Inventors: Anna M. C. F. Castelijns, Stein; Henricus J. Arts, Sittard, both of Netherlands

[73] Assignee: DSM N.V., Netherlands

[21] Appl. No.: 983,556

[22] PCT Filed: Aug. 7, 1991

[86] PCT No.: PCT/NL91/00148

§ 371 Date: May 21, 1993

§ 102(e) Date: May 21, 1993

[87] PCT Pub. No.: WO92/02505

PCT Pub. Date: Feb. 20, 1992

[30] Foreign Application Priority Data

Aug. 8, 1990 [NL] Netherlands ................ 9001786

[51] Int. Cl.6 ................. C07D 213/08; C07D 213/09; C07D 213/12
[52] U.S. Cl. ..................................... 546/250; 546/290
[58] Field of Search ........................ 546/250

[56] References Cited

PUBLICATIONS

K. Takabe, et al, Tetrahedron Letters, No. 49, Dec. 1975, pp. 4375–4376.
M. Komatsu, et al., J. Org. Chem. 1984, vol. 49, pp. 2691–2699.
D. A. Evans, et al., Tetrahedron Letters, No. 26, No. 32, pp. 3787–3790; Aug. 1985.
B. Unterhalt, Chem. Abs., vol. 73, p. 329, 87581u; Oct. 26, 1970.
B. Unterhalt, et al., Chem. Abs, vol. 105, p. 563 208557f; Dec. 08, 1986.
B. Unterhalt, et al., Chem. Abs., vol. 106, p. 568 66838t; Mar. 02, 1987.
C. Hickson, et al, J. Chem. Soc., Perkin Trans. I, 1984, pp. 1569–1572.

*Primary Examiner*—Alan L. Rotman
*Attorney, Agent, or Firm*—Cushman Darby & Cushman

[57] ABSTRACT

Process for the preparation of substituted pyridines by allowing 1-aza-1,3-butadienes to react, in the presence of a catalytic amount of secondary amine and acid, with an aldehyde or ketone, and new 1-aza-1,3-butadienes which are used in this process. Said pyridines can be obtained in high yield in a simple process with a short reaction time. The 1-aza-1,3-butadiene can, if so desired, be prepared in situ from an imine and an aldehyde.

19 Claims, No Drawings

PROCESS FOR THE PREPARATION OF SUBSTITUTED PYRIDINES VIA 1-AZA-1,3-BUTADIENES AND THE 1-AZA-1,3-BUTADIENE INTERMEDIATES

The invention relates to a process for the preparation of a substituted pyridine by reaction of a 1-aza-1,3-butadiene.

A process of this type for the preparation of pyridines is disclosed by Komatsu et al. (*J. Org. Chem.* 49, pp. 2691–2699 (1984)). They prepare asymmetric 3,5-substituted pyridines by allowing 1 equivalent of enamine and 1 equivalent of imine to react to form a 1-aza-1,3-butadiene. This product then reacts in the course of 20–24 hours at 200° C. with another enamine to form an asymmetrically substituted pyridine. The yield varies, depending on the substituents, between 23% and 73%.

Symmetrical 3,5-substituted pyridines are prepared by allowing 2 equivalents of enamine to react in the presence of acid at 200° C. for 9 hours with 1 equivalent of imine. This gives pyridines in a yield, depending on the substituents, of 67 to 87%. In this case the 1-aza-1,3-butadiene is formed in situ from the enamine and the imine.

This preparation process has various disadvantages, The production of symmetrical pyridines proceeds via a 3-step synthesis, that is to say the synthesis of, respectively, the imine, the enamine and the pyridine. Asymmetrically substituted pyridines are prepared via a 4-step synthesis, that is to say synthesis of, respectively, the imine, the enamine, the 1-aza-1,3-butadiene and the pyridine. The reaction time for the formation of the pyridine is long. The enamine is usually prepared by reaction of a secondary amine with an aldehyde. However, this preparation frequently results in low yields, especially if the process is carried out using reactive aldehydes which are not sterically hindered. Problems in the preparation of enamines are described, inter alia, in Whitesell and Whitesell (Synthesis, July 1983, page 517–536). They give a yield of 26% for the formation of the enamine from acetaldehyde and N-butyl-N-isobutylamine. They explain this as follows: "The low yield in the preparation of the enamine from acetaldehyde described above was very probably the consequence of the occurrence of competitive condensation reactions and is typical of the results to be expected in the use of reactive aldehydes which are not sterically hindered."

In the preparation of the enamine, equivalent amounts of secondary amine and aldehyde are used. For the formation of 1 equivalent of pyridine, 2 equivalents of enamine, so also 2 equivalents of secondary amine, are needed. Since secondary amines are often expensive, it makes the reaction economically unattractive. The fact that the preparation of the enamine frequently proceeds with a low yield, as a result of which an unnecessarily large amount of secondary amine and aldehyde are consumed, does not make the reaction economically attractive either.

The object of the invention is to avoid the abovementioned disadvantages.

This is achieved according to the invention in that a pyridine according to formula 1

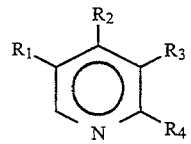

formula 1 where $R_1$ may be H or $R_1$ and $R_3$ can independently be chosen from (cyclo)alkyl, alkenyl, aryl, carboxyalkyl, carboxyaryl, aryloxy, alkoxy, arylthio, arylsulphonyl, $NR'R''$ with 1–20 C-atoms, and halogens, where $R'$ and $R''$ can independently be chosen from H, (cyclo)alkyl and aryl, and $R_2$ can be chosen from H, aryl, alkenyl, and (cyclo)alkyl with 1–20 C-atoms, and only 1 of the groups $R_1$ and $R_2$ may be H, $R_4$ is chosen from H, (cyclo)alkyl, aryl, carboxyalkyl and carboxyaryl with 1–20 C-atoms or $R_3$ and $R_4$ form together with the C-atoms to which they are attached a cycloalkyl-group with 4–8 C-atoms, is formed by allowing the 1-aza-1,3-butadiene according to formula 2

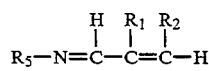

formula 2 where $R_5$ is a OH, alkyl, aryl or alkoxy group with 1–20 C-atoms and $R_1$ and $R_2$ have the meaning described above, to react, in the presence of a catalytic amount of secondary amine and acid, with an aldehyde or ketone according to formula 3

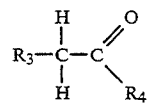

formula 3 where $R_3$ and $R_4$ have the meaning described above.

$R_1$, $R_2$, $R_3$ and $R_4$ usually contain 1–20 C atoms and may optionally be substituted. Possible substituents on $R_1$, $R_2$, $R_3$ and $R_4$ are, for example, halogen, —OH, —SH, (cyclo)alkyl, aryl, aryloxy, alkoxy, carboxyalkyl, carboxyaryl, $NO_2$, $SO_2$ and $NR'R''$, where $R'$ and $R''$ can independently be chosen from H, alkyl and aryl. $R_5$ is usually an alkyl or aryl group having 1–20 C atoms, such as, for example, tertiary butyl, isopropyl and benzyl, tertiary butyl being preferred, or an hydroxy group or an alkoxy group with 1–20 C atoms which may be unsaturated or aromatic such as for example (chloro)allyl.

The molar ratio of 1-aza-1,3-butadiene to aldehyde or ketone which is used in this reaction is not critical and is preferably between 1:1 and 1:3.

Symmetrically substituted pyridines according to formula 4

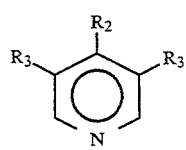

formula 4 can be formed by allowing the imine according to formula 5

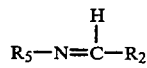

formula 5 where $R_2$ and $R_5$ have the abovementioned meaning, to react, in the presence of a catalytic amount of secondary amine and acid, with an aldehyde according to formula 3, where $R_4$ is hydrogen and $R_3$ has the abovementioned meaning. It is assumed that the 1-aza-1,3-butadiene is formed in situ and immediately further reacts to give a symmetrically substituted pyridine. The invention also relates to this direct process of preparing symmetrical pyridines.

The 1-aza-1,3-butadiene can also be prepared by allowing an amine $R_5$—$NH_2$ wherein $R_5$ has the above mentioned meaning to react with an alpha, beta-unsaturated aldehyde according to formula 6

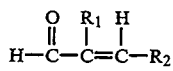

formula 6 where $R_1$ and $R_2$ have the abovementioned meaning, with the proviso that when $R_5$ represents an alkyl or aryl group $R_2$ is not H. After the addition of an aldehyde or ketone according to formula 3 and a catalytic amount of secondary amine and acid, pyridines are formed. The reaction with ketones is preferentially performed with amines with $R_5$ is hydroxy or alkoxy.

The ratio between the various reactants can vary. If formation of symmetrical pyridines from 1-aza-1,3-butadiene formed in situ is opted for, a minimum of 2 equivalents of the aldehyde according to formula 3 per equivalent of imine according to formula 5 is needed, on the basis of the reaction mechanism, to achieve optimum results. Preferably, between 2 and 4 equivalents are added.

The amount of secondary amine can be chosen within wide limits. It has been found that higher concentrations of secondary amine usually produce higher yields. However, secondary amines are frequently expensive. When determining the amount of secondary amine, economic considerations also play a role, in addition to yield considerations, Preferably, the molar ratio of aldehyde:secondary amine is chosen between 5:1 and 15:1. Many secondary amines are suitable for use as catalyst. Cyclic amines, in particular piperidine, are preferred.

The choice of the acid is not critical. Suitable acids are, for example, inorganic acids, carboxylic acids or sulphonic acids, such as hydrochloric acid, acetic acid and p-toluenesulphonic acid. The molar ratio of amine:acid can vary within wide limits and is usually chosen between 0.4 and 50.

If the 1-aza-1,3-butadiene is prepared from an amine and an alpha,beta-unsaturated aldehyde, the molar ratio of amine:unsaturated aldehyde is generally chosen around 1:1. Usually, a small excess of amine (between 1.0 and 1.2 equivalents per equivalent of the unsaturated aldehyde) is added. In theory, equal amounts of 1-aza-1,3-butadiene and aldehyde or ketone are needed for the formation of the pyridine from 1-aza-1,3-butadiene and aldehyde or ketone. In practice, an excess of aldehyde or ketone is usually added.

The reaction temperature can vary within wide limits. Usually said temperature is chosen between 100 and 300° C. A reaction temperature between 180 and 220° C. is preferred. In this temperature range the reaction is complete within 2 hours in virtually all cases.

It has been found that the process according to the invention provides the following advantages. Substituted pyridines can be prepared in a simpler process, with fewer reaction steps, by direct use of the readily accessible aldehyde or ketone, instead of the enamine, which is sometimes difficult to prepare. As a result, only a catalytic amount of secondary amine is required. Moreover, the overall yield relative to the aldehyde or ketone increases appreciably. The reaction time for the pyridine formation is appreciably reduced.

A number of pyridines occur in natural products. The invention provides a process with which substituted pyridines, some of which are new, can be prepared in a simple manner. These pyridines can be used in various fields.

Alkylpyridines can, for example, be used as precursors for pyridinemonocarboxylic and -dicarboxylic acids, which show a direct relationship with nicotine derivatives.

The invention also relates to the new compounds having the general formula

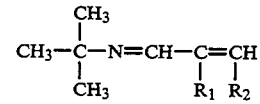

where $R_1$ is H and $R_2$ is ethyl, isopropyl, n-butyl, (cyclo)alkyl having 5–20 C atoms, alkoxy having 1–20 C atoms, a thioalkyl, thioaryl, alkylamino or arylamino group having 1–20 C or atoms phenyl substituted with hydroxy, (cyclo)alkyl having 1–5 C atoms, halogen, or where $R_2$ is H and $R_1$ is n-propyl, alkyl having 4–20 C atoms, alkoxy having 2–20 C atoms, thioalkyl, alkylamino or arylamino group having 1–20 C atoms or phenyl optionally substituted with hydroxy, (cyclo)alkyl having 1–5 C atoms, alkoxy having 1–5 C atoms, halogen, or where $R_1$ and $R_2$ each independently represent (cyclo)alkyl having 4–20 C atoms, alkoxy having 2–20 C atoms, halogen, a thioalkyl, thioaryl, alkylamino or arylamino group having 1–20 C atoms or phenyl optionally substituted with hydroxy, (cyclo)alkyl having 1–5 C atoms, alkoxy having 1–5 C atoms, halogen and the new compounds having the general formula

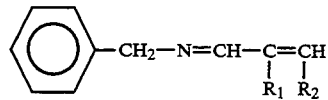

where $R_1$ is H and $R_2$ is (cyclo)alkyl having 2–20 C atoms, alkenyl having 3–20 C atoms, alkoxy having 1–20 C atoms, a thioalkyl, thioaryl, alkylamino or arylamino group having 1–20 C atoms or phenyl substituted with hydroxy, (cyclo)alkyl having 1–5 C atoms, alkoxy having 2–5 C atoms, halogen or where $R_2$ is H and $R_1$ is (cyclo)alkyl having 2–20 C atoms, alkoxy having 2–20 C atoms, alkenyl having 2–20 C atoms, a thioalkyl, thioaryl, alkylamino or arylamino group having 1–20 C atoms or phenyl optionally substituted with hydroxy, (cyclo)alkyl having 1–5 C atoms, alkoxy having 1–5 C atoms, halogen or where $R_1$ and $R_2$ each independently represent (cyclo)alkyl having 2–20 C atoms, alkoxy having 1–20 C atoms, alkenyl having 2–20 C atoms, halogen, a thioalkyl, thioaryl, alkylamino or arylamino group having 1–20 C atoms or phenyl optionally substituted with hydroxy, (cyclo)alkyl having 1–5 C atoms, alkoxy having 1–5 C atoms, halogen, and the new compounds having the general formula

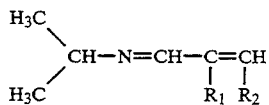

where $R_1$ is H and $R_2$ is (cyclo)alkyl having 2–20 C atoms, alkenyl having 5–20 C atoms, alkoxy having 1–20 C atoms a thioalkyl, thioaryl, alkylamino or arylamino group having 1–20 C atoms or phenyl substituted with hydroxy, (cyclo)alkyl having 1–5 C atoms, alkoxy having 1–5 C atoms, halogen or in which $R_2$ is H and $R_1$ is (cyclo)alkyl having 3–20 C atoms, alkenyl having 2–7 C atoms, alkoxy having 1–20 C atoms, a thioalkyl, thioaryl, alkylamino or arylamino group having 1–20 C atoms or phenyl optionally substituted with hydroxy, (cyclo)alkyl having 1–5 C atoms, alkoxy having 1–5 C atoms, halogen or where $R_1$ and $R_2$ each independently represent (cyclo)alkyl having 3–20 C atoms, alkenyl having 2–20 C atoms, alkoxy having 1–20 C atoms, a thioalkyl, thioaryl, alkylamino or arylamino group having 1–20 C atoms or phenyl optionally substituted with hydroxy, (cyclo)alkyl having 1–5 C atoms, alkoxy having 1–5 C atoms, halogen, and the new compounds having the general formula

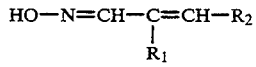

where $R_1$ is H and $R_2$ is (cyclo)alkyl having 2–20 C atoms, alkenyl having 2–20 C atoms, alkoxy having 1–20 C atoms, halogen, a thioalkyl, thioaryl, alkylamino or arylamino group having 1–20 C atoms or phenyl substituted with hydroxy, (cyclo)alkyl having 1–5 C atoms, alkoxy having 1–5 C atoms, halogen, with the proviso that phenyl is not substituted in the p-position with methyl, isopropyl, methoxy, Cl or Br, or where $R_2$ is H and $R_1$ is (cyclo)alkyl having 3–20 C atoms, alkoxy having 1–20 C atoms, alkenyl having 2–20 C atoms, halogen, a thioalkyl, thioaryl, alkylamino or arylamino group having 1–20 C atoms or phenyl optionally substituted with hydroxy, (cyclo)alkyl having 1–5 C atoms, alkoxy having 1–5 C atoms, halogen, or where $R_1$ and $R_2$ each independently represent (cyclo)alkyl having 2–20 C atoms, alkenyl having 2–20 C atoms, alkoxy having 1–20 C atoms, halogen, a thioalkyl, thioaryl, alkylamio or arylamino group having 1–20 C atoms or phenyl optionally substituted with hydroxy, (cyclo)alkyl having 1–5 C atoms, alkoxy having 1–5 C atoms, halogen with the proviso that $R_1$ and $R_2$ are not at the same time given by $R_1=C_2H_5$ or $C_3H_7$ and $R_2=$ a phenylgroup in the p-position substituted with $CH_3$, $OCH_3$, F, Cl or Br, and the new compounds having the general formula

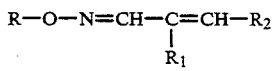

where R is (cyclo)alkyl with 1–20 C atoms and $R_1$ and $R_2$ each independently represent H, (cyclo)alkyl having 1–20 C atoms, alkoxy having 1–20 C atoms, alkenyl having 2–20 C atoms, halogen a thioalkyl, thioaryl, alkylamino or arylamino group having 1–20 C atoms or phenyl optionally substituted with hydroxy, (cyclo)alkyl having 1–5 C atoms, alkoxy having 1–5 C atoms, halogen, with the proviso that R, $R_1$ and $R_2$ are not at the same time given by R is H and $R_2$ is phenyl or phenyl in the p-position substituted with methyl, methoxy or halogen, or R is $CH_3$, $R_1$ is $CH_3$ and $R_2$ is phenyl; These compounds are formed as an intermediate in the process according to the invention.

Alkyl, alkenyl or aryl groups may optionally be substituted with the abovementioned substituents.

The invention is further elucidated by means of the following examples, without being restricted by these.

The NMR data are given as follows. The shift is indicated in ppm downfield with respect to TMS. The multiplicity is indicated as s (singlet), d (doublet), t (triplet), q (quartet), sept. (septet), m (multiplet) and b (broad signal). Aromatic protons are given as pyr. (protons on pyridine ring) and Ph. (protons on phenyl ring).

EXAMPLE I

Preparation of 1-tert-butyl-4-phenyl-1-aza-1,3-butadiene 20.3 grams of t-butylamine (0.28 mol) was metered over a period of 16 minutes to 33.0 grams of cinnamaldehyde (0.25 mol) during stirring and cooling. The mixture was left to stand overnight at room temperature. 150 ml of butanone was then added to the crude reaction mixture to enable the water formed during the reaction to be evaporated azeotropically. The mixture was evaporated on a rotary evaporator. The residue consisted of 45.6 grams of product having a purity of 98%. Yield 96%.

$^1$H NMR: $\delta=1.29$ ppm, s, 9H, 3 $CH_3$ $\delta=6.80$ ppm, s (b), and $\delta=6.89$ ppm, s (b), 2H, $2CH=\delta=7.10-7.55$ ppm, m, 5H, Ph. $\delta=7.93$ ppm, t, 1H, $CH=N$ Preparation of 3-methyl-4-phenylpyridine, from 1-tert-butyl-4-phenyl-1-aza-1,3-butadiene and propanal 3.7 grams (20 mmols) of the 1-aza-1,3-butadiene prepared above, 3.5 grams of propanal (60 mmols), 0.7 gram of piperidine (8.2 mmols), 4.4 grams of toluene (solvent) and 1.0 gram of a solution of 1.2 grams of acetic acid in 48.8 grams of toluene (0.4 mmol of acetic acid) were added together in a Cr-Ni steel autoclave with a capacity of about 15 ml. The latter was heated for 2 hours in an oil bath at a temperature of 200° C. After 2 hours the reaction mixture was cooled in air. The not optimized yield of 3-methyl-4-phenylpyridine was 34% (GC analysis). The reaction mixture was purified by means of a fractional distillation, by which means product having a purity of 86% was obtained. Further purification took place by dissolving the distillate in hexane and by passing HCl gas through this solution, as a result of which the pyridine HCl salt precipitated. The salt was filtered off. A dilute sodium hydroxide solution was then added, after which the aqueous solution was extracted with dichloromethane. After evaporating off the dichloromethane, product having a purity of 98.8% was obtained.

$^1$H NMR: $\delta=2.23$ ppm, s, 9H, 3 $CH_3$ $\delta=7.03$ ppm, d, 1H, pyr. $\delta=7.1-7.5$ ppm, m (b), 5H, Ph. $\delta=8.38$ ppm, d, 2H, pyr.

EXAMPLE II

Preparation of the imine of t-butylamine and formaldehyde (t-butylmethyleneimine as triazine trimer)

295.0 grams of t-butylamine (4.0 mols) was metered to 120.0 grams of paraformaldehyde (4.0 mols), with cooling. ⅓ of the amine was added in a single amount. The stirrer was then started. The remainder of the amine was added over a period of 1¼ hours, after which the mixture was stirred for a further ½ hour at room temperature. The crude reaction mixture was transferred to a separating funnel, in which said mixture separated in the course of about 2 hours into an aqueous phase and a turbid organic phase. The organic phase was filtered through filter earth. The clear filtrate, 327.6 grams, consisted of 98% pure imine (in the form of triazine trimer). Yield 94%.

Preparation of 3,5-dimethylpyridine from t-butylmethyleneimine and propanal 211.8 grams of the t-butylmethyleneimine prepared above (98% pure, 2.44 mols), 424.5 grams of propanal (7.32 mols), 292.8 grams of toluene (solvent), 76.1 grams of piperidine (0.9 mol) and 103.6 grams of acetic acid (1.73 mols) were mixed with cooling in an ice/water bath while being stirred. Piperidine and acetic acid were added in small portions in connection with the release of heat. The mixture was transferred to an autoclave and heated at 200° C. for 3 hours (heating-up time about 45 min.). The reaction mixture was cooled to room temperature. It was then washed with 400 grams of a 20% (wt) NaOH solution in water. The aqueous phase contained no 3,5-dimethylpyridine. The organic phase contained 100.0 grams of product (not optimized yield 38.3%). The volatile components were distilled off from the organic phase under atmospheric pressure through a column having 20 actual plates. The residue was distilled under vacuum through a column having 20 actual plates. This resulted in 78.9 grams of 3,5-dimethylpyridine having a purity of 98% (distillation yield 79%, overall yield 30.2%). Boiling point 104°-107° C. (102 mm Hg). In this case the 1-aza-1,3-butadiene was formed in situ from the imine and the aldehyde, after which the pyridine formation took place.

$^1$H NMR: $\delta=2.28$ ppm, s, 6H, 2 CH$_3$ $\delta=7.23$ ppm, m, and $\delta=8.75$ ppm, m, 3H, pyr.

EXAMPLE III

Preparation of 3,5-dimethylpyridine from t-butylmethyleneimine and propanal 1.7 grams of the t-butylmethyleneimine prepared in Example II (20 mmols), 3.5 grams of propanal (60 mmols), 0.8 gram of piperidine (9.4 mmols), 6.1 grams of toluene (solvent) and 1.0 gram of a solution of 1.2 grams of acetic acid in 48.8 grams of toluene (0.4 mmol of acetic acid) were added together in a Cr—Ni steel autoclave with a capacity of about 15 ml. The latter was heated for 2 hours in an oil bath at a temperature of 200° C. After 2 hours the reaction mixture was cooled in air. The yield of 3,5-dimethylpyridine was 50% (GC analysis).

EXAMPLE IV

Preparation of 3,5-diethylpyridine from t-butylmethyleneimine and butanal 1.7 grams of the t-butylmethyleneimine (20 mmols) prepared in Example II, 4.3 grams of butanal (60 mmols), 0.7 gram of piperidine (8.2 mmols), 5.6 grams of toluene (solvent) and 1.0 gram of a solution of 1.2 grams of acetic acid in 48.8 grams of toluene (0.4 mmol of acetic acid) were added together in a Cr—Ni steel autoclave with a capacity of about 15 ml. The latter was heated for 2 hours in an oil bath at a temperature of 200° C. After 2 hours the reaction mixture was cooled in air. The not optimized yield of 3,5-diethylpyridine was 55% (GC analysis). The crude product was purified by means of vacuum distillation. Boiling point 86°-88° C. (10 mm Hg), purity 84%. Further purification took place by precipitating the distilled product as the HCl salt in hexane. The salt was filtered off and then dissolved in water and the solution was neutralised using 33% strength by weight NaOH solution in water. The aqueous solution was then extracted with dichloromethane. This resulted in a product having a purity of 98.5%.

$^1$H NMR: $\delta=1.20$ ppm, t, 6H, 2 CH$_3$ $\delta=2.58$ ppm, q, 4H, 2 CH$_2$ $\delta=7.20$ ppm, t, and 8.18 ppm, d, 3H, pyr.

EXAMPLE V

Preparation of 3,5-di-isopropylpyridine from t-butylmethyleneimine and isovaleraldehyde 1.7 grams of t-butylmethyleneimine (20 mmols), 5.2 grams of isovaleraldehyde (60 mmols), 0.7 gram of piperidine (8.2 mmols), 4.7 grams of toluene (solvent) and 1.0 gram of a solution of 1.2 grams of acetic acid in 48.8 grams of toluene (0.4 mmol of acetic acid) were added together in each of 4 Cr—Ni steel autoclaves with a capacity of about 15 ml. The latter were heated for variable periods in an oil bath at a temperature of 200° C. The reaction mixtures were then cooled in air. The not optimized yield was 47% after 1 hour, 51% after 2 hours, 53% after 3 hours and 56% after 4 hours (GC analysis). The crude product was purified by means of distillation, which resulted in a number of fractions having a 3,5-di-isopropylpyridine content which varied between 10 and 80%. The 3,5-di-isopropylpyridine crystallized out in the fractions having a content higher than 38%. Product having a purity of 93% was obtained by filtering off.

Melting point 36.5°-38.5° C. $^1$H NMR: $\delta=1.25$ ppm, d, 12H, 4 CH$_3$ $\delta=2.88$ ppm, sept., 2H, 2 CH $\delta=7.28$ ppm, t, and 8.20 ppm, d, 3H, pyr.

EXAMPLE VI

Preparation of the imine of t-butylamine and benzaldehyde 36.0 grams (0.5 mol) of t-butylamine was metered to 52.2 grams of benzaldehyde (0.5 mol) over a period of 60 minutes during stirring. After all of the t-butylamine had been added, the mixture was stirred for a further 1 hour at room temperature. A further 14.6 grams (0.2 mol) of t-butylamine was then added, after which the mixture was stirred for 1½ hours at room temperature. The reaction mixture was transferred to a separating funnel and 100 ml of diethyl ether was added to allow better separation of the organic and the aqueous phase. The organic layer was dried over MgSO$_4$. The latter was filtered off. The filtrate was evaporated in a rotary evaporator. This yielded 65.0 grams of product having a purity of 99%. Yield 82%.

$^1$H NMR: $\delta=1.34$ ppm, s, 9H, 3 CH$_3$ $\delta=7.18-7.40$ ppm, m, and 7.56–7.78 ppm, m, 5H, Ph. $\delta=8.16$ ppm, s, 1H, CH=N Preparation of 3,5-diphenylpyridine from t-butylmethyleneimine and phenylacetaldehyde 10.3 grams of the t-butylmethyleneimine prepared above (98% pure; 0.12 mols), 51.0 grams of phenylacetaldehyde (85% pure; 0.36 mols), 13.4 grams of toluene (solvent), 4.52 grams of piperidine (0.053 mols) and 0.20 grams of acetic acid (0.003 mols) were mixed with cooling in an ice/water bath while being stirred. The mixture was transferred to an autoclave and heated at 200° C. for 1½ hours. After cooling to roomtemperature the separated crystals were filtered and washed with suction. After drying of the solid 19.0 grams of 98% pure 3,5-diphenylpyridine was obtained (The yield was 68% without any optimization). In this case the 1-aza-1,3-butadiene was formed in situ from the imine and the aldehyde, after which the pyridine formation took place.

$^1$H NMR: $\delta=7.4-7.7$ ppm, m, 10H, 2 Ph $\delta=8.05$ ppm, t, 1H, 4-H $\delta=8.83$ ppm, d, 2H, 2-H and 6-H

EXAMPLE VII

Preparation of formaldoxime (as trimer)

64.2 grams of a solution of NaOH in water (50%; 0.802 mols) was added to a stirred solution of 66.1 grams of hydroxylamine sulfate (0.805 mols) in 134.1 grams of water with cooling (t ≈25° C.). Then, a solution of 22.2 grams of formaldehyde (0.74 mols) in 37.8 grams of water was added, immediately followed by the addtion of 100 ml of ether. After separation of the two layers, the water phase was extracted 3 times with ether. The combined organic phases were dried (CaCl$_2$) and the solvent was evaporated in vacuum. The residue (30.0 grams) consisted of 97% pure formaldoxime (in the form of its trimer). Yield: 87%.

Preparation of 3,5-dimethylpyridine from formaldoxime and propanal 6.3 grams of the formaldoxime prepared above (97% pure; 0.14 mols), 23.2 grams of propanal (0.4 mols), 52.2 grams of toluene (solvent), 5.24 grams of piperidine (0.062 mols) and 0.36 grams of piperidine. HCl salt (0.003 mols) were mixed with cooling in an icewater both while being stirred. The mixture was transferred to an autoclave and heated at 200° C. for 1½ hours. After cooling to room temperature the reaction mixture was analyzed. The not optimized yield of 3,5-dimethylpyridine was 26% (GC analysis).

EXAMPLE VIII

Preparation of cinnamaldehyde oxime 53.3 grams of cinnamaldehyde (0.40 mols) was added to a solution of 39.1 grams of hydroxylamine sulfate (0.48 mols) in 79.5 grams of water. The mixture was cooled in an icewater bath to 3° C. Then a solution of 17.7 grams of NaOH (0.44 mol) in 17.7 grams of water was added over a period of 25 minutes. The formed cinnamaldehyde oxime precipitated. The reaction mixture was warmed to roomtemperature and the crude product was filtered. After recrystallization from toluene pure cinnamaldehyde oxime was obtained as white crystals. Yield: 70%.

Preparation of 4-phenyl-5,6,7,8-tetrahydroquinoline 13.9 grams of the cinnamaldehyde oxime prepared according to the above described procedure (0.09 mols), 28.5 grams of cyclohexanon (0.29 mols), 30.3 grams of toluene (solvent), 3.44 grams of piperidine (0.040 mols) and 0.259 grams of piperidine. HCl salt (0.002 mols) were mixed with cooling in an icewater bath while being stirred. The mixture was transferred to an autoclave and heated at 200° C. for 1½ hours. After cooling to room temperature the mixture was analyzed. The not optimized yield of 4-phenyl-5,6,7,8-tetrahydroquinoline was 34% (GC-analysis).

EXAMPLE IX

Preparation of methacroleine oxime 32.7 grams of hydroxylamine hydrochloride (0.47 mols) was dissolved in 66.4 grams of water. This solution was cooled in an icewater bath to 3°-5° C. and 32.0 grams of methacroleine (0.45 mols) was added with stirring. Subsequently 35.7 grams of a solution of NaOH in water (50%; 0.45 mol) was added at 4° C. over a period of 1 hour. Then the reaction mixture was brought at room temperature and extracted with ether. The combined organic phases were dried (MgSO$_4$) and the solvent was removed under reduced pressure. The residue (36.7 grams) consisted of pure methacroleine oxime (93% in ether); Yield: 89%.

Preparation of 3,5-dimethylpyridine from methacroleine oxime and propanal 13.0 grams of the methacroleine oxime prepared according to the above described procedure (93% in ether; 0.14 mol), 22.0 grams of propanal (0.38 mols), 46.5 grams of toluene (solvent), 4.93 grams of piperidine (0.058 mols) and 0.35 grams of piperidine. HCl salt (0.003 mols) were mixed with cooling in an icewater bath while being stirred. The mixture was transferred to an autoclave and heated at 200° C. for 1½ hours. After cooling to room temperature the mixture was analysed. The not optimalized yield of 3,5-dimethylpyridine was 28% (GC-analysis).

EXAMPLE X

Preparation of 3,5-dimethylpyridine from O-methylformaldoxime and propanal 8.3 grams of O-methylformaldoxime (0.14 mols), prepared according to the procedure of Jensen et al. (*Acta Chem. Scand.*, 31, 28 (1977), 23.2 grams of propanal (0.40 mols) 52.2 grams of toluene (solvent), 5.33 grams of piperidine (0.063 mols) and 0.18 grams of acetic acid (0.003 mols) were mixed with cooling in an icewater bath while being stirred. The mixture was transferred to an autoclave and heated at 200° C. for 1½ hours. After cooling to room temperature the reaction mixture was analysed. The not optimized yield of 3,5-dimethylpyridine was 28% (GC analysis).

We claim:

1. A process for the preparation of a substituted pyridine by reaction of a 1-aza-1,3-butadiene wherein, a pyridine represented by formula 1

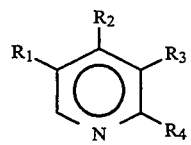

(1)

wherein $R_1$ is H or $R_1$ and $R_3$ can be a 1–20 carbon atom group independently selected from the group consisting of (cyclo)alkyl, aryl, and alkoxy and $R_2$ is H or a 1–20 carbon atom group independently selected from the group consisting of aryl and (cyclo)alkyl, wherein only one of $R_1$ and $R_2$ may be H, $R_4$ is selected from the group consisting of H, aryl having 6 to 20 carbon atoms and (cyclo)alkyl with 1–20 carbon atoms, or $R_3$ and $R_4$ form together with the C atoms to which they are attached a cycloalkyl group with 4–8 C-atoms, is formed by allowing an 1-aza-1,3-butadiene represented by formula (2)

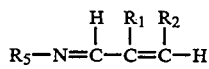

(2)

wherein $R_5$ is a OH, alkyl having 1–20 carbon atoms, aryl having 6–20 carbon atoms or alkoxy group having 1–20 C-atoms and $R_1$ and $R_2$ have the meaning described above, to react, in the presence of a catalytic amount of secondary amine and acid, with an aldehyde or ketone represented by formula (3)

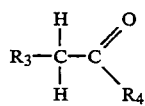

(3)

wherein $R_3$ and $R_4$ have the meaning described above.

2. A process according to claim 1, wherein the process is conducted at a molar ratio of 1-aza-1,3-butadiene:aldehyde or ketone of between 1:1 and 1:3.

3. A process according to claim 1, wherein $R_1$ is independently selected from group consisting of hydrogen, methyl, ethyl, isopropyl and phenyl.

4. A process according to claim 1, wherein $R_3$ is independently selected form the group consisting of methyl, ethyl, isopropyl and phenyl.

5. A process according to claim 1, wherein the reaction is conducted at a temperature of 100° C. to 300° C.

6. A process according to claim 1, wherein the reaction is conducted at a temperature of 180° C. to 220° C.

7. A process according to claim 1, wherein the acid is a carboxylic acid or sulphonic acid.

8. A process according to claim 1, wherein the acid is selected from the group consisting of hydrochloric acid, acetic acid and p-toluenesulphonic acid.

9. A process according to claim 1, wherein the secondary amine has a cyclic structure.

10. A process according to claim 1, wherein the secondary amine is piperidine.

11. A process for the preparation of a symmetrical pyridine represented by formula 4:

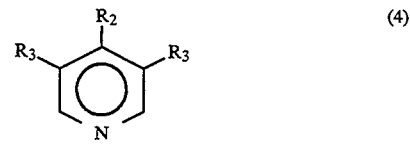

(4)

wherein $R_3$ is a 1–20 carbon group selected from the group consisting (cyclo)alkyl, aryl, alkoxy, $R_2$ is selected from the group consisting of H, aryl having 6 to 20 carbon atoms, and (cyclo)alkyl with 1–20 C-atoms, wherein an imine represented by formula 5:

(5)

wherein $R_2$ has the above-mentioned meaning and % is an OH, alkyl having 6 to 20 carbon atoms, aryl having 6 to 20 carbon atoms or alkoxy group with 1–20 C-atoms, is allowed to react, in the presence of a catalytic amount of a secondary amine and an acid, with an aldehyde represented by formula (3)

(3)

wherein $R_3$ has the above-mentioned meaning.

12. A process according to claim 11, wherein the process is conducted at a molar ratio of imine:aldehyde of between 1:2 and 1:4.

13. A process according to claim 11, wherein the secondary amine has a cyclic structure.

14. A process according to claim 11, wherein the processes conducted at a temperature between 100° C. and 300° C.

15. A process according to claim 11, wherein the temperature is between 180° C. and 220° C.

16. A process according to claim 11, wherein the acid is a carboxylic acid or sulphonic acid.

17. A process according to claim 11, wherein the acid is selected from the group consisting of hydrochloric acid, acetic acid and p-toluenesulphonic acid.

18. A process according to claim 11, wherein the secondary amine is piperidine.

19. A process according to claim 1, wherein $R_5$ is hydroxyl or methoxy.

* * * * *